United States Patent [19]

Liu et al.

[11] Patent Number: 5,147,727
[45] Date of Patent: Sep. 15, 1992

[54] ARYLOXY POLYVINYL ETHERS

[75] Inventors: Kou-Chang Liu, Wayne; Fulvio J. Vara, Chester; James A. Dougherty, Pequannock, all of N.J.

[73] Assignee: ISP Investments Inc., Wilmington, Del.

[21] Appl. No.: 772,408

[22] Filed: Oct. 7, 1991

Related U.S. Application Data

[62] Division of Ser. No. 475,535, Feb. 6, 1990, Pat. No. 5,082,874.

[51] Int. Cl.$^5$ ............................................. B32B 27/00
[52] U.S. Cl. ..................................... 428/500; 522/31; 522/100; 522/170; 427/53.1; 427/54.1
[58] Field of Search .............. 428/500; 427/54.1, 53.1; 522/31, 100, 170

[56] References Cited

U.S. PATENT DOCUMENTS

| | | | |
|---|---|---|---|
| 4,017,652 | 4/1977 | Gruber | 427/54 |
| 4,370,358 | 1/1983 | Hayes et al. | 427/54.1 |
| 4,657,779 | 4/1987 | Gaske | 427/54.1 |
| 4,994,299 | 2/1991 | Stein et al. | 427/54.1 |

Primary Examiner—Marion E. McCamish
Assistant Examiner—Mark A. Chapman
Attorney, Agent, or Firm—Marilyn J. Maue; Joshua J. Ward

[57] ABSTRACT

This invention relates to aryloxy polyvinyl ethers having the formula

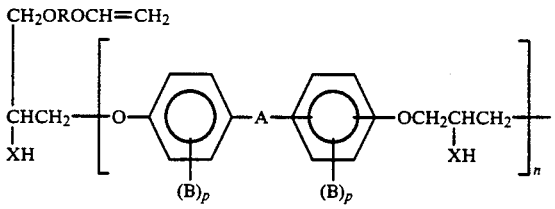

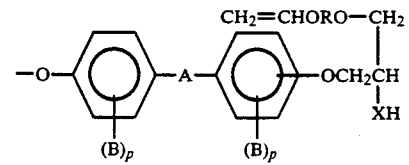

wherein R is a radical having from 2 to 20 carbon atoms and is selected from the group of alkylene, alkyleneoxy alkylene, polyalkyleneoxy alkylene, arylene, alkarylene, alkarylalkylene and aralkylene; X is oxygen or sulfur; A is branched or linear alkylene having from 1 to 20 carbon atoms; B is halo or lower alkyl; n has a value of from 1 to 6 and p has a value of from 0 to 4. The invention also relates to the preparation and use of said aryloxy divinyl ethers.

13 Claims, No Drawings

ARYLOXY POLYVINYL ETHERS

This is a division of application Ser. No. 475,535, filed Feb. 6, 1990, now U.S. Pat. No. 5,082,874

In one aspect this invention relates to novel, polyfunctional aryloxy polyvinyl ethers and to the process for their preparation. In another aspect the invention relates to monomeric, oligomeric and polymeric materials which are rapidly curable in the presence of air or oxygen by cationically induced irradiation to strongly adhesive and chemically resistant coatings. In still another aspect the invention relates to polyfunctional resins which are suitable as adhesives, inks or as chemical intermediates.

BACKGROUND OF THE INVENTION

Certain radiation curable coatings and films such as those formed from the acrylates are in great demand; however, since acrylate monomers are not conducive to cationically induced radiation curing, they require more costly free radical systems which are oxygen inhibited unless effected in an inert atmosphere, generally under a blanket of nitrogen. Although formulation with a photoinitiator which undergoes bimolecular reaction with a hydrogen donor minimizes the inhibitory effect of air, this benefit is realized at the expense of a greatly reduced cure rate. Also, it is found that polymerization or curing in free radical systems ceases almost immediately upon removal from the source of radiation; thus, the cured product usually contains significant amounts of unpolymerized components.

Finally, it is noted that the unsubstituted acrylates are sensitizers and skin irritants as well as being carcinogenic, so that specialized safety precautions must be taken to protect operators from exposure. Although alkoxylation has lessened irritancy of the acrylates, their carcinogenic properties are not reduced.

The inherent deficiencies of the acrylate systems can be partially overcome by the use of epoxy resins. Epoxy resins can be polymerized by normal radiation techniques using cationic photoinitiators such as iodonium, sulfonium and ferrocene salts, hexafluorophosphate, hexafluoroantemonate and hexafluoroarsonate to produce a tack free film. Although in such formulations tack free products are almost immediately obtained, polymerization of the mixture is incomplete. It is well known that the polymerization of epoxy resins is extremely slow and requires as much as several days to achieve their ultimate physical properties. Thus, thermal curing is often employed to increase the rate of polymerization.

Certain allyl compounds also have been used as coatings; however these monomers and their oligomers are not readily curable by cationic radiation. Thermal curing is generally required to increase the rate of polymerization. While allyl ethers such as polyethylene glycols are curable by UV light, they require a free radical initiated reaction which proceeds at a slow rate, generally over a period of from 2 to 10 hours in order to reach completion.

Accordingly, it is an object of this invention to overcome the above deficiencies and to provide a commercially feasible and economical process for producing radiation curable compounds which are homopolymerizable and which may be combined with other polymers or monomers not normally curable by radiation, particularly cationically promoted radiation curing.

Another object is to develop a monomer having the beneficial properties of the acrylates but which is amenable to radiation curing at a rapid rate by cationically induced polymerization which is not oxygen inhibited and which permits continued polymerization after removal from the source of radiation exposure.

Another object is to provide film forming compounds which have excellent resistance to abrasion and chemicals such as solvents, acids and basis.

Another object is to provide a simple and economical process for the copolymerization of the present compounds disposed as protective coatings on a substrate.

Still another object is to provide compounds capable of forming hydrogels by hydrolysis.

Still another object is to provide photoresist compounds capable of high image resolution upon exposure to a source of radiation.

These and other objects will become apparent from the following description and disclosure.

THE INVENTION

In accordance with this invention there is provided an aryloxy polyvinyl ether having the formula

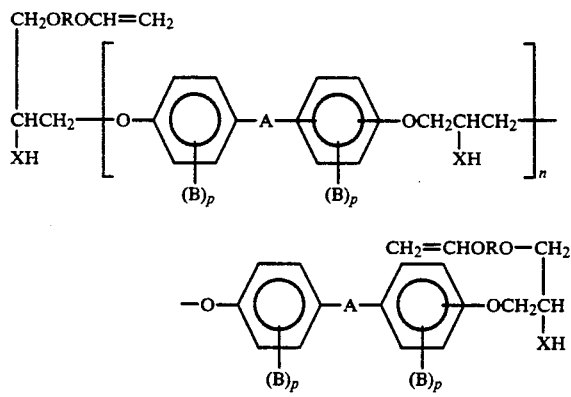

wherein R is a linear, branched or cyclic radical having from 2 to 20 carbon atoms and is selected from the group of alkylene, alkyleneoxy alkylene, polyalkyleneoxy alkylene, arylene, alkarylene, alkarylalkylene and aralkylene; X is oxygen or sulfur; A is branched or linear alkylene having from 1 to 20 carbon atoms; B is halo or lower alkyl; n has a value of from 1 to 20 and p has a value of from 0 to 4. The invention also relates to the preparation and use of said aryloxy divinyl ethers.

Unlike their aryloxy monovinyl ether or epoxy counterparts, the present compound are able to form a cross-linked network of aryloxy vinyl ether homopolymer. This characteristic provides a much higher crosslinked density which results in significantly harder, more chemically resistant films and coatings.

Preferred compounds of this invention are those wherein X is oxygen; A is $>C(CH_3)_2$; p is zero; n has a value of from 1 to 4 and R is a radical having from 2 to 8 carbon atoms.

The above divinyl ethers are synthesized by reacting a hydroxyvinyl ether with a diepoxide of a bisphenol such as bisphenol A epoxy resin, eg. EPON 828, supplied by Shell Chemical Co. or DER 332, supplied by Dow Chemical Co. or a bisphenol F epoxy resin, eg. EPON DPL 826 supplied by Shell Chemical Co. The reaction is effected according to the following equation.

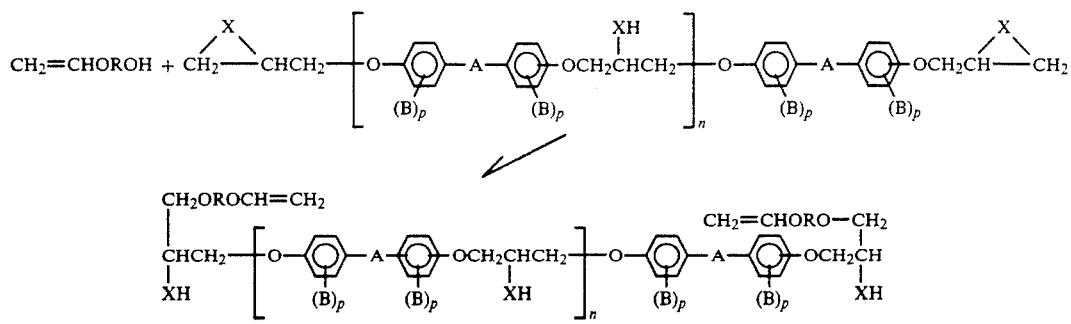

The synthesis reaction can be carried out in the presence of air or in the absence of oxygen under a blanket of inert gas. Generally, the present condensation reaction is carried out at a temperature of between about 100° and about 175° C. under atmospheric pressure for a period of from 0.5 to 200 hours. Preferred reaction parameters include a temperature of from about 120° to about 160° C. for a period of from about 2 to about 100 hours.

The reaction is also conducted in the presence of a base catalyst such as particulate sodium, potassium, or lithium metal, sodium or potassium hydroxide or hydride. The catalyst is present in an amount of from about 0.01 to about 2 wt. %, preferably from about 0.1 to about 1 wt. % of the total mixture. When the reactants and products included herein are liquids, they are generally synthesized in the absence of diluents or solvents which are otherwise required for more viscous or solid reactants. Suitable solvents include toluene, xylene, triethylene glycol dimethyl ether, N-methylpyrrolidone and the like. Such solvents can be employed in concentrations up to about 50% of the reaction mixture.

The hydroxy vinyl ether reactant and the phenylic coreactant of the present process are generally employed in a mole ratio of from about 1:1 to about 10:1, preferably from about 1.05:1 to about 3:1.

Suitable hydroxylated vinyl ether reactants include the mono vinyl ether of cyclohexanedimethanol, tetra(-hydroxyethyl) vinyloxy hexane, (2-hydroxyethyl) vinyl ether, (3-hydroxypropyl) vinyl ether, the monovinyl ether of 3-ethyl-1,6-hexanediol, (4-hydroxybutyl) vinyl ether, 6-hydroxyhexyl vinyl ether, the monovinyl ether of 2-methyl-1,8-octanediol, (vinyloxy) cresol, vinyloxymethyl cyclohexyl methanol and alkoxylated derivatives thereof containing from 1 to 6 ethyleneoxy or propyleneoxy units. Suitable coreactants include 1,3-{bis4-{2-[4-(2,3-epoxypropoxy)phenyl]prop-2-yl}phenoxy}-2-propanol, 1,3-bis{4-[4-(2,3-epoxypropoxy)benzyl]benzyl]-phenoxy}-2-propanol poly(phenylalkylphenoxy-2-propanol-3-oxy)epoxy-propoxy epoxypropoxyphenylalkylphenyl and the like.

The products of this invention can be homopolymerized to hard chemically resistant films and coatings which have good substrate substantivity. Alternatively, the present compounds can be mixed with alkenyl ether, alkenyl ester, epoxide or acrylate monomers or polymers to impart rapid radiation curing properties in the presence of a cationic photoinitiator. Cross-linking co-polymerizations can be carried out in the presence of air to produce highly desirable films and coatings which retain the desirable properties of both monomers or their polymerized derivatives. Curable compositions containing between about 0 and about 80% of a vinyl ether, an epoxide, an acrylate or a methacrylate comonomer or a polymer thereof and between about 20% and about 100% of the present aryloxy divinyl ether in the presence of from about 0.05 to about 5 wt. % of a cationic photoinitiator are suitable radiation curable coatings which are polymerized by exposure to UV light, electron beam, laser emission or other sources of radiation. Between about 2 and about 50 wt. % of the present product is employed with from about 0.1 to about 5 wt. % of a conventional cationic photoinitiator, such as an onium salt, for example the triphenyl sulfonium salt of phosphorous hexafluoride, diphenyl iodium salt, tetrazolium chloride, phenyl onium salts or aryl alkyl onium salts and the like. Usually, exposure for less than one second is sufficient to provide a completely cross-linked homopolymer. UV light radiation dosages at room temperature of from about 100 to about 1500 milli J/cm$^2$ are effective and dosages of from about 200 to about 600 milli J/cm$^2$ are preferred. Equivalent dosages for curing are employed when using alternative sources of radiation. For example, curing with electron beam radiation can be carried out at between about 0.5 and about 20 Mrads, preferably between about 1 and about 10 Mrads. Specific techniques for radiation curing are well known, thus further amplification is not required.

The present products can be mixed with a vinyl ether, epoxide, acrylate or methacrylate monomer or polymer to incorporate and combine the advantages of instant compounds with the beneficial properties of those coating materials which otherwise would not be amenable to rapid cationic radiation curing. Some examples of monomers or polymers with which the present products can be combined to form coatings include the mono- and di- vinyl ethers of di-, tri-or tetra- ethylene or propylene glycol; ethylene divinyl ether, butylene divinyl ether, hexylene divinyl ether, dodecylene divinyl ether, hexadecylene divinyl ether, eicosylene divinyl ether, benzene divinyl ether and corresponding thioethers; hexanediol diacrylate or methacrylate, pentaerythritol triacrylate, trimethaerylate and bis(epoxyalkoxy)phenyl alkanes and other functional monomers and polymers which possess properties beneficial in durable protective coatings.

The homopolymerized and copolymerized products of this invention have high resistance to solvents, acids and bases and form hard abrasion resistant films and coatings, possessing good substrate substantivity. The individual products of this invention, as monomers or oligomers or as mixtures thereof are also useful as chemical intermediates and as materials which, upon hydrolysis, are capable of forming hydrogels. Also, because of their high radiation sensitivity, the present compounds are suitable as photoresist materials.

Having generally described the invention, reference is now had to the accompanying examples which illustrate preferred embodiments thereof but which are not to be construed as limiting to the scope of the invention as more broadly set forth above and in the appended claims.

EXAMPLE

Hydroxybutyl vinyl ether (1900 g), EPON 828 epoxy resin (345.6 g) and potassium hydroxide (0.5 g) were charged to a three liter flask equipped with a mechanical stirrer, thermometer, nitrogen inlet and a condenser adapted with a drying tube. The solution was heated at 120° C. for 24 hours and 150° C. for 48 hours, after which 400 g of the resulting solution was transferred to a one liter flask. Unreacted hydroxybutyl vinyl ether heated to 160° C., after which the propane pressure was readjusted to 100 psig and acetylene (100 psig) was added to initiate the vinylation. After 4 hours, the reaction was halted and 46% (642 g) of product was then recovered in 99% purity by twice distilling the crude mixture in a 15 plate Oldershaw column at 103° C. under 4 mm Hg.

The cyclohexanedimethanol monovinyl ether product (469.3 g), EPON 828 epoxy resin (150 g) and potassium hydroxide (85% pellets, 0.5 g) were charged into a flask equipped as described in Example 1. The solution was heated to 150° C. for 48 hours and then cooled to room temperature. The resulting crude product (300 g), 500 ml of toluene and 2 g of magnesium silicate were then transferred into a 1 liter flask wherein the mixture was stirred for 1 hour at room temperature and then filtered. After toluene and unreacted cyclohexane methanol vinyl ether were stripped off, the divinyl ether of EPON 828 resin product having the structure

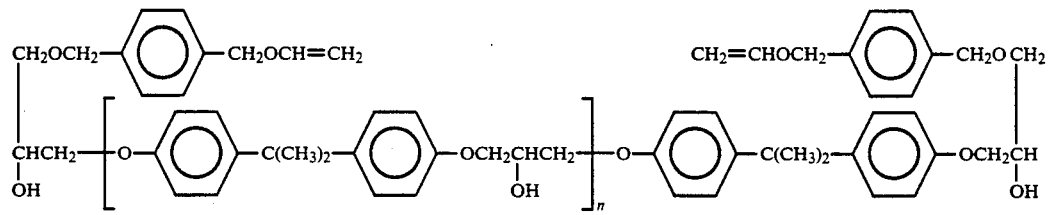

was stripped off and 300 ml of toluene was added. The resulting solution was washed five times with 300 ml of water, dried over calcium sulfate and filtered. After stripping off toluene solvent, the substantially pure divinyl ether product having the structure:

was obtained as a pale yellow jelly.

EXAMPLE 3

Hydroxyethyl vinyl ether (431.5 g), EPON 828 resin (282 g) and potassium hydroxide (0.5 g, 85% pellets)

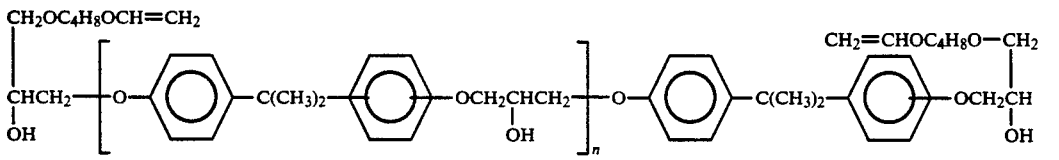

was obtained as a yellow viscous oil.

The above product was then evaluated for a radiation cured coating by coating in about 0.15 mil thickness on an aluminum panel and then exposing for less than 1 second at room temperature to 400 milli J/cm$^2$ radiation from 2 medium pressure mercury vapor lamps. The cured coating had strong adhesion to the substrate and had excellent resistance to chemical attack from acids and bases.

EXAMPLE 2

Cyclohexanedimethanol (1802.6 g) and potassium hydroxide (85% pellets, 36 g) were charged into a one gallon stainless steel autoclave. The autoclave was initially purged with nitrogen at room temperature and then twice at 110° C. under 20 mm Hg vacuum for 0.5 hour. Propane (100 psig) was added, the solution was were charged into a 1 liter flask equipped as described as in Example 1. The solution was heated and held at reflux for 56 hours, after which the solution was cooled to room temperature, stirred with 5 g of magnesium silicate for 1 hour and filtered. Unreacted, excess hydroxyethyl vinyl ether was stripped off and the divinyl ether of EPON 828 product having the structure:

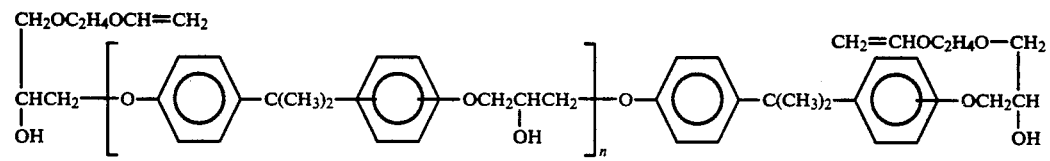

was obtained as a pale yellow oil.

EXAMPLE 4

Hydroxybutyl vinyl ether (648 g), EPON epoxy resin DPL-862 (498 g) and potassium hydroxide (0.5 g) were charged into a two liter flask equipped as described in Example 1. The solution was heated at 120° C. for 24 hours and then at 158° C. for 48 hours. Magnesium silicate (10 g) was added to the solution, the resulting mixture was stripped for 1 hour at 40° C. and then filtered. The unreacted excess hydroxybutyl vinyl ether was stripped off and the divinyl ether product having the structure:

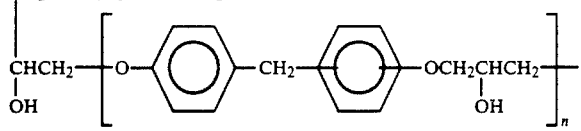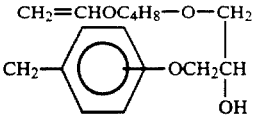

was recovered as a yellow viscous oil.

What is claimed is:

1. A substrate having a cured surface coating of an effective protective amount of the cured product of a composition containing between about 0 and about 80 wt. % of a monomer or oligomer selected from the group of an epoxide, an acrylate or methacrylate, an olefin and an aliphatic vinyl ether and between about 20 and about 100 wt. % of an aryloxy polyvinyl ethers having the formula wherein R is a radical having from 2 to 20 carbon atoms and is selected from the group of alkylene, alkyleneoxy alkylene, polyalkyleneoxy alkylene, arylene, alkarylene, aslkarylalkylene and aralkylene; X is oxygen or sulfur; A is branched or linear alkylene having from 1 to 20 carbon atoms; V is halo or lower alkyl; n has a value of from 1 to 6 and p has a value of from 0 to 4, said composition containing up to about 5 wt. % of a cationic photoinitiator.

2. A substrate having a cured surface coating of an effective protective amount of the product of claim 1 wherein X of the aryloxy polyvinyl ether is oxygen.

3. A substrate having a cured surface coating of an effective protective amount of the product of claim 2 wherein R of the aryloxy polyvinyl ether is a radical having from 2 to 8 carbon atoms.

4. The substrate of claim 3 wherein said aryloxy polyvinyl ether has the formula:

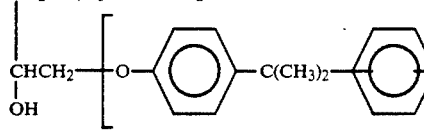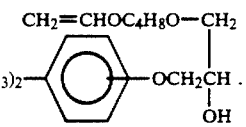

5. The substrate of claim 3 wherein said aryloxy polyvinyl ether has the formula:

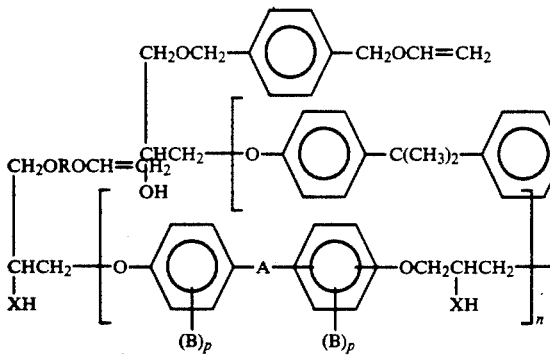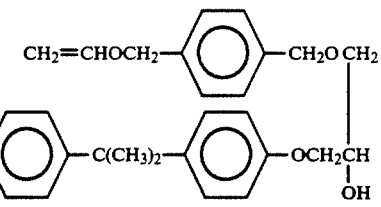

6. The substrate of claim 3 wherein p of the aryloxy polyvinyl ether is zero.

7. The substrate of claim 3 wherein n of the aryloxy polyvinyl ether has a value of from 1 to 4.

8. The substrate of claim 1 wherein the aryloxy polyvinyl ether has the formula

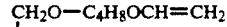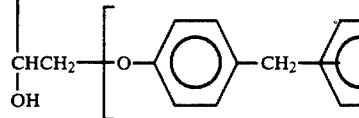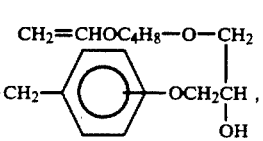

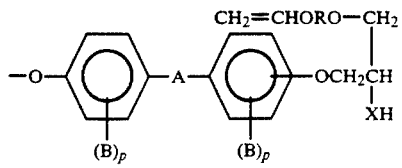

9. The substrate of claim 1 wherein said cured product is crosslinked.

10. The substrate of claim 1 wherein A of the aryloxy polyvinyl ether is selected from the group of —CH$_2$— and —C(CH$_3$)$_2$—.

11. The process of (a) coating a substrate with an effective chemical protective amount of a composition containing between about 0 and about 80 wt. % of a monomer or oligomer selected from the group of an epoxide, an acrylate or methacrylate, an olefin and an aliphatic vinyl ether and between about 20 and about 100 wt. % of an aryloxy polyvinyl ethers having the formula

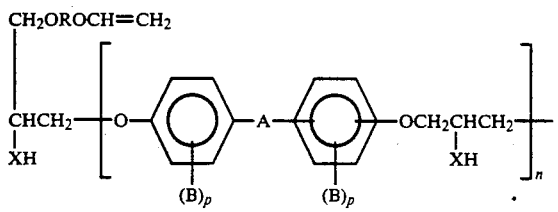

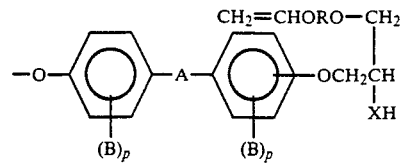

wherein R is a radical having from 2 to 20 carbon atoms and is selected from the group of alkylene, alkyleneoxy alkylene, polyalkyleneoxy alkylene, arylene, alkarylene, alkarylalkylene and aralkylene; X is oxygen or sulfur; A is branched or linear alkylene having from 1 to 20 carbon atoms; B is halo or lower alkyl; n has a value of from 1 to 6 and p has a value of from 0 to 4, said composition containing up to about 5 wt. % of a cationic photoinitiator, and (b) curing said coating by exposure to a source of radiation.

12. The process of claim 11 wherein the aryloxy polyvinyl ether is selected from the group of

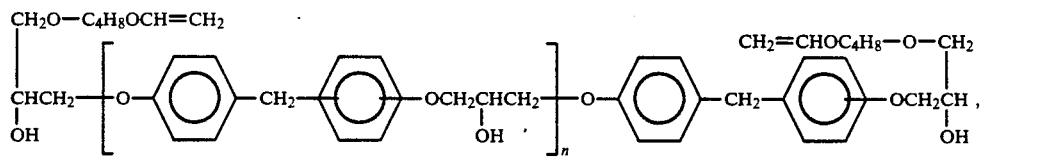

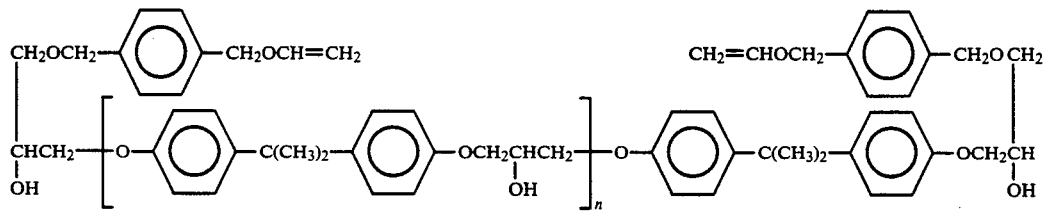

and

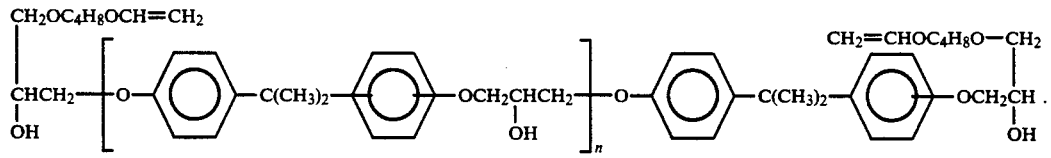

13. The process of claim 11 wherein the product of the process is crosslinked.

* * * * *